(12) United States Patent
Matsumoto et al.

(10) Patent No.: US 8,258,344 B2
(45) Date of Patent: Sep. 4, 2012

(54) PLASTIC CRYSTAL

(75) Inventors: Hajime Matsumoto, Ikeda (JP);
Zhi-Bin Zhou, Ikeda (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 586 days.

(21) Appl. No.: 12/448,624

(22) PCT Filed: Dec. 26, 2007

(86) PCT No.: PCT/JP2007/074943
§ 371 (c)(1),
(2), (4) Date: Jun. 26, 2009

(87) PCT Pub. No.: WO2008/081811
PCT Pub. Date: Jul. 10, 2008

(65) Prior Publication Data
US 2010/0069667 A1 Mar. 18, 2010

(30) Foreign Application Priority Data
Dec. 28, 2006 (JP) .................................. 2006-353658

(51) Int. Cl.
C07C 211/63 (2006.01)
C07C 217/08 (2006.01)
H01M 6/04 (2006.01)
H01G 9/02 (2006.01)

(52) U.S. Cl. ........ 564/291; 564/293; 564/296; 429/188; 361/504

(58) Field of Classification Search ................... 564/291, 564/293, 296; 429/188; 361/504
See application file for complete search history.

(56) References Cited

U.S. PATENT DOCUMENTS
4,537,843 A * 8/1985 Shishikura et al. ........... 429/339
2007/0099079 A1 5/2007 Matsumoto et al.

FOREIGN PATENT DOCUMENTS
JP 2002-063934 * 2/2002
JP 2006-236829 9/2006
WO 2005/063773 7/2005

OTHER PUBLICATIONS

Zhou et al., "A New Class of Hydrophobic Ionic Liquids: Trialkyl(2-methoxyethyl)ammonium Perfluoroethyltrifloroborate", Chemistry Letters, vol. 33, No. 7 (2004).*

International Search Report dated Feb. 26, 2008 in the International (PCT) Application PCT/JP2007/074943 of which the present application is the U.S. National Stage.
Isobel Davidson et al., Investigation of Phase Diagram of Plastic Crystal Electrolytes B Succinonitrile and Li [CF3S02]2N, Meet, Abstr.—Electrochem. Soc., vol. 602, p. 249, 2006.
Douglas R. MacFarlane et al., "Lithium-doped plastic crystal electrolytes exhibiting fast ion conduction for secondary batteries", Nature, vol. 402, pp. 792-794, 1999.
D.R. MacFarlane et al., "Pyrrolidinium Imides: A New Family of Molten Salts and Conductive Plastic Crystal", J. Phys. Chem. B, vol. 103, pp. 4164-4170, 1999.
Maria Forsyth et al., "Lithium doped N-methyl-N-ethylpyrrolidinium bis(trifluromethanesulfonyl)amide fast-ion conducting plastic crystals", J. Matter Chem., vol. 10, pp. 2259-2265, 2000.
Zhi-Bin Zhou et al., "Low-Melting, Low-Viscous, Hydrophobic Ionic Liquids: Aliphatic Quaternary Ammonium Salts with Perfluoroalkyltrifluoroborates", Chem. Eur. J., vol. 11, pp. 752-766, 2005.
The 14$^{th}$ International Meeting on Lithium Batteries Meeting Abstracts IMLB 2008 Abstract #464 "Highly Conductive Organic Ionic Plastic Crystal Based on Perfluoroalkyl Trifluoroborate", 2008.

* cited by examiner

*Primary Examiner* — Peter G O Sullivan
(74) *Attorney, Agent, or Firm* — Wenderoth, Lind & Ponack, L.L.P.

(57) ABSTRACT

The present invention relates to a conductor having high conductivity and electrochemical stability, which is in a solid state over a practically wide temperature range. Specifically disclosed is a plastic crystal containing a compound represented by Formula (I) or (IA) below:

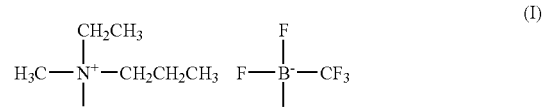

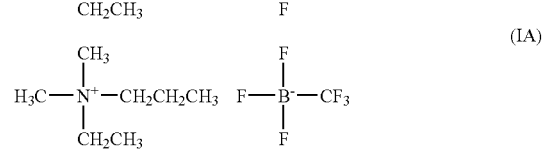

and at least one compound $[BF_3(CF_3)]$ salt represented by Formula (II):

$$M^{n+}[BF_3(CF_3)^-]_n \qquad (II)$$

wherein M is an alkaline metal, alkaline earth metal, aluminum or H; and when M is an alkaline metal or H, n is 1; when M is an alkaline earth metal, n is 2; and when M is aluminum, n is 3.

13 Claims, 13 Drawing Sheets

□ indicates only $N_{1223}[CF_3BF_3]$
◇ indicates after doping with iodide ion ($N_{1223}[CF_3BF_3]_{0.67}I_{0.33}$)
■ indicates after further doping with iodine ($N_{1223}[CF_3BF_3]_{0.67}$ $I_{0.23}$ $I_3$ $_{0.1}$)

PLASTIC CRYSTAL

TECHNICAL FIELD

The present invention relates to a plastic crystal having a plastic crystalline phase over a wide temperature range around room temperature, an electrochemical device containing the plastic crystal, and an electrolyte for a dye-sensitized solar cell.

BACKGROUND ART

Recently, a plastic crystal having high conductivity has drawn public attention as a new type of electrolyte material because such a plastic crystal offers the potential of solidifying the electrolyte used in electrochemical devices, including primary and secondary batteries, such as lithium secondary batteries; dye-sensitized solar cells; and fuel cells. Known materials are limited in terms of having a practical level of high conductivity and/or a usable temperature range.

A plastic crystal is a mesophase that is formed by a first-order solid to solid phase transition at a temperature lower than the melting point of the molecule or ionic compound. In this mesophase, the molecules or ions that form the plastic crystalline phase are characterized by their long-range order regarding position, and rotational or disorder for orientation. This type of disorder results in the formation of defects. However, such defects not only create liquid-like characteristics that allow doped ions or matrix-forming ions to quickly migrate, but also render these materials with plastic-like mechanical characteristics. A lithium ion conductive plastic crystal that is usable as a solid electrolyte for lithium batteries first became known through a report showing that a lithium-ammonium double salt exhibits high conductivity. It was reported that the conductivity was dramatically increased by two or more orders of magnitude by doping the plastic crystalline phase of a pyrrolidinium-TFSI salt with a small amount of lithium bis(trifluoromethanesulfonyl)imide (TFSI$^-$). As a result of this, plastic crystalline electrolytes have recently been drawing attention (Non-Patent Documents 1 to 3).

Plastic crystals used as a solid matrix for dissolving lithium salt can be divided into two categories: molecules and ions. A plastic crystalline electrolyte having a high conductivity of $10^{-4}$ to $10^{-3}$ Scm$^{-1}$ at room temperature has been obtained by doping a plastic crystalline phase with succinonitrile [NC(CH$_2$)$_2$CN]. Initial reports indicated the possibility of using that plastic crystalline electrolyte as a solid electrolyte material for lithium batteries; however, such a material contains a large amount of combustible molecular compounds and therefore has drawbacks (e.g., volatility and combustibility) that are similar to those of conventional liquid electrolytes. In contrast, an organic ion plastic crystal (OIPC) has a relatively low melting point (no higher than 100° C.), and exhibits excellent ionic liquid characteristics, such as noncombustibility. These advantages were fully understood, but the heretofore reported lithium ion conductive OIPC has a low ion conductivity at room temperature and this hinders the lithium ion conductive OIPC from being practically used in lithium batteries.

The present inventors reported that N,N-diethyl-N-methyl-N-(n-propyl)ammonium trifluoromethyl trifluoroborate was a plastic crystal; however, its electroconductivity at room temperature was as low as about $10^{-6}$ Scm$^{-1}$ (Non-Patent Document 4).

Non-Patent Document 1: D. R. MacFarlane, J. Huang, M. Forsyth, Nature 402 (1999) 792.

Non-Patent Document 2: D. R. MacFarlane, P. Meakin, J. Sun, N. Amini, M. Forsyth, J. Phys. Chem. B 103 (1999) 4164.

Non-Patent Document 3: M. Forsyth, J. Huang, D. R. MacFarlane, J. Mater. Chem. 10 (2000) 2259.

Non-Patent Document 4: Z.-B. Zhou, H. Matsumoto, K. Tatsumi, Chem. Eur. J. 11 (2005) 752.

DISCLOSURE OF THE INVENTION

Problem to be Solved by the Invention

The two lithium ion doped type pyrazolium plastic crystals have a high conductivity of $10^{-4}$ Scm$^{-1}$ at room temperature. However, because their plastic crystalline phases appear in a narrow temperature range and pyrazolium cation has a low cathode stability, their value for use in lithium batteries is lessened. Accordingly, there is still interest in developing a lithium ion conductor-based OIPC having high conductivity and electrochemical stability that is in a solid state in a wide range of highly practical temperatures.

An object of the present invention is to provide a novel plastic crystal.

Means for Solving the Problem

The present inventors conducted extensive research on various OIPCs. As a result, the present inventors found that by adding a BF$_3$(CF$_3$) salt represented by M$^{n+}$[BF$_3$(CF$_3$)$^-$]$_n$, and if necessary, further adding iodide ions (I$^-$) and triiodide ions (I$_3^-$) to N,N-diethyl-N-methyl-N-(n-propyl)ammonium trifluoromethyl trifluoroborate represented by Formula (I) (hereafter referred to as N$_{1223}$ [CF$_3$BF$_3$]) or N-ethyl-N,N-dimethyl-N-(n-propyl)ammonium trifluoromethyl trifluoroborate (hereafter referred to as N$_{1123}$[CF$_3$BF$_3$]), an electroconductivity as high as about $10^{-4}$ Scm$^{-1}$ at room temperature can be achieved while maintaining plastic crystal characteristics.

The present inventors also found that N,N,N-trimethyl-N-(methoxymethyl)ammonium pentafluoroethyl trifluoroborate (hereafter referred to as N$_{111,101}$[C$_2$F$_5$BF$_3$]) is a plastic crystal.

An object of the present invention is to provide plastic crystals, electrochemical devices (in particular, batteries such as lithium secondary batteries, and fuel cells) and an electrolyte for use in solar cells (in particular, dye-sensitized solar cells) as described below.

Item 1. A plastic crystal containing a compound represented by Formula (I) or (IA) below:

and at least one [BF$_3$(CF$_3$)] salt represented by Formula (II):

wherein M is an alkaline metal, alkaline earth metal, aluminum or H; and when M is an alkaline metal or H, n is 1; when M is an alkaline earth metal, n is 2; and when M is aluminum, n is 3.

Item 2. The plastic crystal according to Item 1, which contains 1 to 10 mol % of the [BF$_3$(CF$_3$)] salt.

Item 3. The plastic crystal according to Item 1, which contains 2.5 to 5 mol % of the [BF$_3$(CF$_3$)] salt.

Item 4. A plastic crystal comprising a compound represented by Formula (I) or (IA) below:

and a compound represented by Formula (III) or (IIIA) below:

wherein X is a hydroxide ion, halogenated compound ion, or pseudohalogen ion.

Item 5. The plastic crystal according to Item 4, which contains 10 to 50 mol % of a compound represented by Formula (III) or (IIIA).

Item 6. A plastic crystal represented by Formula (IB) below:

Item 7. The plastic crystal according to Item 6, which comprises a compound represented by Formula (IB) below:

and at least one [BF$_3$(C$_2$F$_5$)] salt represented by Formula (IIB):

wherein M is an alkaline metal, alkaline earth metal, aluminum or H; and when M is an alkaline metal or H, n is 1; when M is an alkaline earth metal, n is 2; and when M is aluminum, n is 3.

Item 8. The plastic crystal according to Item 7, which comprises 1 to 10 mol % of the [BF$_3$(C$_2$F$_5$)] salt.

Item 9. The plastic crystal according to Item 7, which comprises 2.5 to 5 mol % of [BF$_3$(C$_2$F$_5$)] salt.

Item 10. A plastic crystal comprising a compound represented by Formula (IB):

and a compound represented by Formula (IIIB):

wherein X represent a hydroxide ion, halogenated compound ion, or pseudohalogen ion.

Item 11. The plastic crystal according to Item 10, which comprises 10 to 50 mol % of the compound represented by Formula (IIIB).

Item 12. An electrochemical device comprising a plastic crystal of any one of Items 1 to 11.

Item 13. An electrolyte for a dye-sensitized solar cell comprising a plastic crystal of Item 4, 5, 10 or 11.

Effect of the Invention

The present invention can provide a plastic crystal having a plastic crystalline phase over a wide temperature range, such as −30° C. to 80° C. (N$_{1223}$[CF$_3$BF$_3$]) or −20° C. to 50° C. (N$_{1123}$[CF$_3$BF$_3$]). This plastic crystal contains a [BF$_3$(CF$_3$)] salt represented by Formula (II), in particular Li[BF$_3$(CF$_3$)], and makes it possible to obtain a plastic crystalline electrolyte exhibiting a conductivity as high as about $10^{-4}$ to $10^{-3}$ Scm$^{-1}$ at room temperature, which can be desirably used as an electrochemical device. By adding, instead of [BF$_3$(CF$_3$)] salt, at least one compound represented by Formula (III), in particular N$_{1223}$I or N$_{1223}$I$_3$, or alternatively N$_{1123}$I or N$_{1123}$I$_3$, the plastic crystalline electrolyte can be suitably used as an electrolyte for solar cells, in particular for dye-sensitized solar cells.

Furthermore, the present invention provides a plastic crystal (N$_{111.101}$[C$_2$F$_5$BF$_3$]) having a plastic crystalline phase over a wide temperature range from −40° C. to 100° C.

BEST MODE FOR CARRYING OUT THE INVENTION

In one preferable embodiment, the plastic crystal of the present invention uses N,N-diethyl-N-methyl-N-(n-propyl) ammonium trifluoromethyl trifluoroborate (hereafter referred to as N$_{1223}$[BF$_3$(CF$_3$]) or N-ethyl-N,N-dimethyl-N-(n-propyl)ammonium trifluoromethyl trifluoroborate (hereafter referred to as N$_{1123}$ [CF$_3$BF$_3$]) and a [BF$_3$(CF$_3$)] salt represented by Formula (II) (for example Li[BF$_3$(CF$_3$)]) and/or at least one compound selected from those represented by Formulae (III) and (IIIA). The anion (BF$_3$(CF$_3$)$^-$) is a known compound and disclosed in, for example, G. A. Molander, B. J. Hoag, Organometallics, 22, (2003) 3313; Zhi-Bin Zhou, Masayuki Takeda, Makoto Ue, J. Fluorine. Chem., 123 (2003) 127. N,N-diethyl-N-methyl-N-(n-propyl)ammonium (N$_{1223}$), N-ethyl-N,N-dimethyl-N-(n-propyl)ammonium (N$_{1123}$), N,N,N-trimethyl-N-(methoxymethyl)ammonium (N$_{111.101}$), and BF$_3$(C$_2$F$_5$)$^-$ are also known compounds. (N$_{111.101}$ is disclosed in Non-Patent Document: H. Matsumoto, et al., Chem. Lett., (2000), 922.)

Examples of usable alkaline metals include Na, K, Li, Cs, etc. Among these, Na, K, and Li are preferable; Na and Li are more preferable; and Li is particularly preferable.

Examples of usable alkaline earth metals include Mg, Ca, Sr, and Ba. Among these, Mg and Ca are preferable; and Mg is particularly preferable.

Examples of usable halogenated compound ions include $F^-$, $Cl^-$, $Br^-$, $I^-$ and like halogenated ions; and $I_3^-$, $Br_3^-$, $I_2Br^-$, $IBr_2^-$ and like polyhalide ions. Among these, Br, I, $I_3^-$, $Br_3^-$, $I_2Br^-$, and $IBr_2^-$ are preferable; and $I^-$ and $I_3^-$ are particularly preferable. These ions can be added to a plastic crystal as a $N_{1223}$ salt, $N_{1123}$ salt, and $N_{111.101}$ salt.

Examples of usable pseudohalogenated ions include $SCN^-$, $SeCN^-$, $OCN^-$, etc.

In one preferable embodiment, the plastic crystal of the present invention can be readily obtained by mixing a compound represented by Formula (I) disclosed in Non-Patent Document 4 with $M[BF_3(CF_3)]$ (M is as defined above) and/or at least one compound represented by $N_{1223}$ salt X (X is as defined above), followed by heating the mixture.

A mixture of $N_{1223}[CF_3BF_3]$ or $N_{1123}[CF_3BF_3]$ and at least one $[BF_3(CF_3)]$ salt represented by Formula (II), and a mixture of $N_{111.101}[C_2F_5BF_3]$ and at least one $[BF_3(C_2F_5)]$ salt represented by Formula (IIB) exhibit excellent properties suitable for use in an ionic plastic crystalline electrolyte. A compound represented by Formula (IIB), wherein M is H (proton), is suitably usable in fuel cells. When M is an alkaline metal, alkaline earth metal or aluminum ion, the compound represented by Formula (IIB) is suitably usable in batteries.

These compounds exhibit a plastic crystalline phase at a temperature of about −30 to 80° C. ($N_{1223}[CF_3BF_3]$), about −20 to 50° C. ($N_{1123}[CF_3BF_3]$), or about −40 to 100° C. ($N_{111.101}[C_2F_5BF_3]$) (this result implies that these compounds are ideally usable as a solid electrolyte at ambient temperatures). Furthermore, these compounds exhibit excellent electroconductivity, i.e., about $10^{-4}$ to $10^{-2}$ $Scm^{-1}$, at room temperature. This plastic crystal is a flexible bulk material that is very soft at room temperature. Therefore, it does not easily break when subjected to slight manual stress.

$N_{111.101}[C_2F_5BF_3]$ also exhibits excellent properties suitable for use as an ionic plastic crystalline electrolyte.

Figure 1:
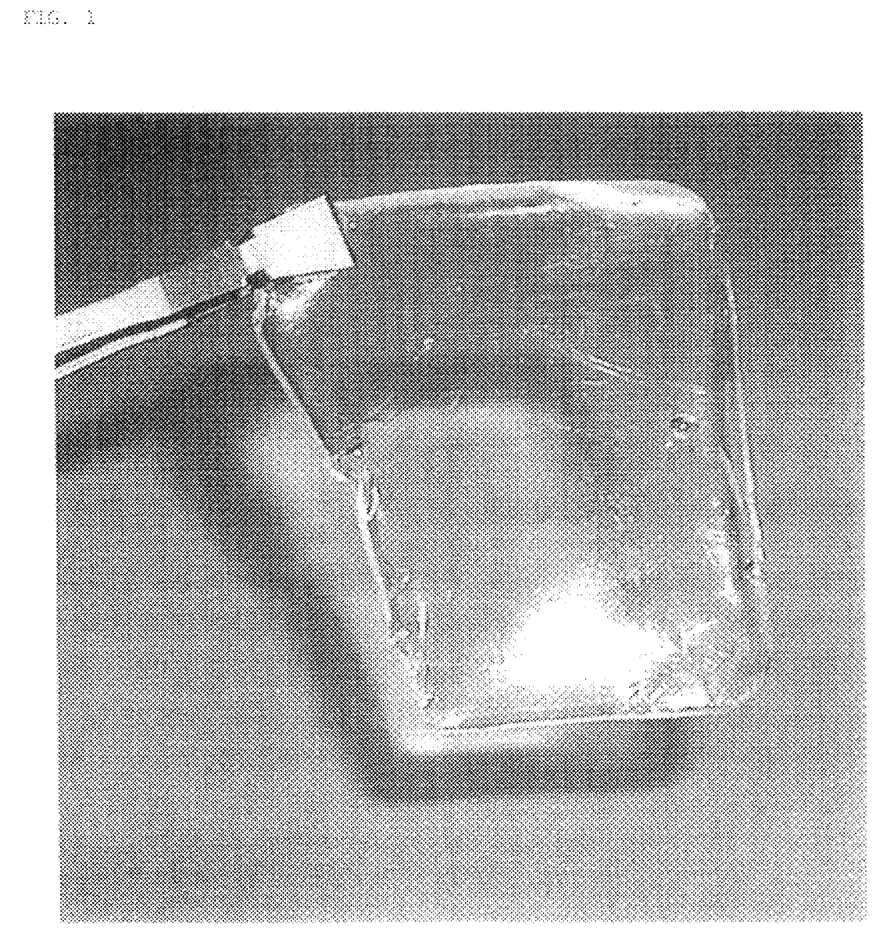
FIG. 1 is a photograph of a freestanding film (having a diameter of about 50 mm) obtained by melting solvent-free N,N-diethyl-N-methyl-N-(n-propyl)ammonium trifluoromethyl trifluoroborate ($N_{1223}$[$CF_3BF_3$]) on a PTFE plate at 100° C., and then cooling it to room temperature.

The plastic crystal of the present invention containing a $[BF_3(CF_3)]$ salt, such as $N_{1223}[CF_3BF_3]$ and $Li[BF_3(CF_3)]$, exhibits a colorless transparent plastic crystalline phase as shown in FIG. 1. Therefore, it is suitably usable for an optical material, a display, etc., in which transparency is required.

Figure 7:
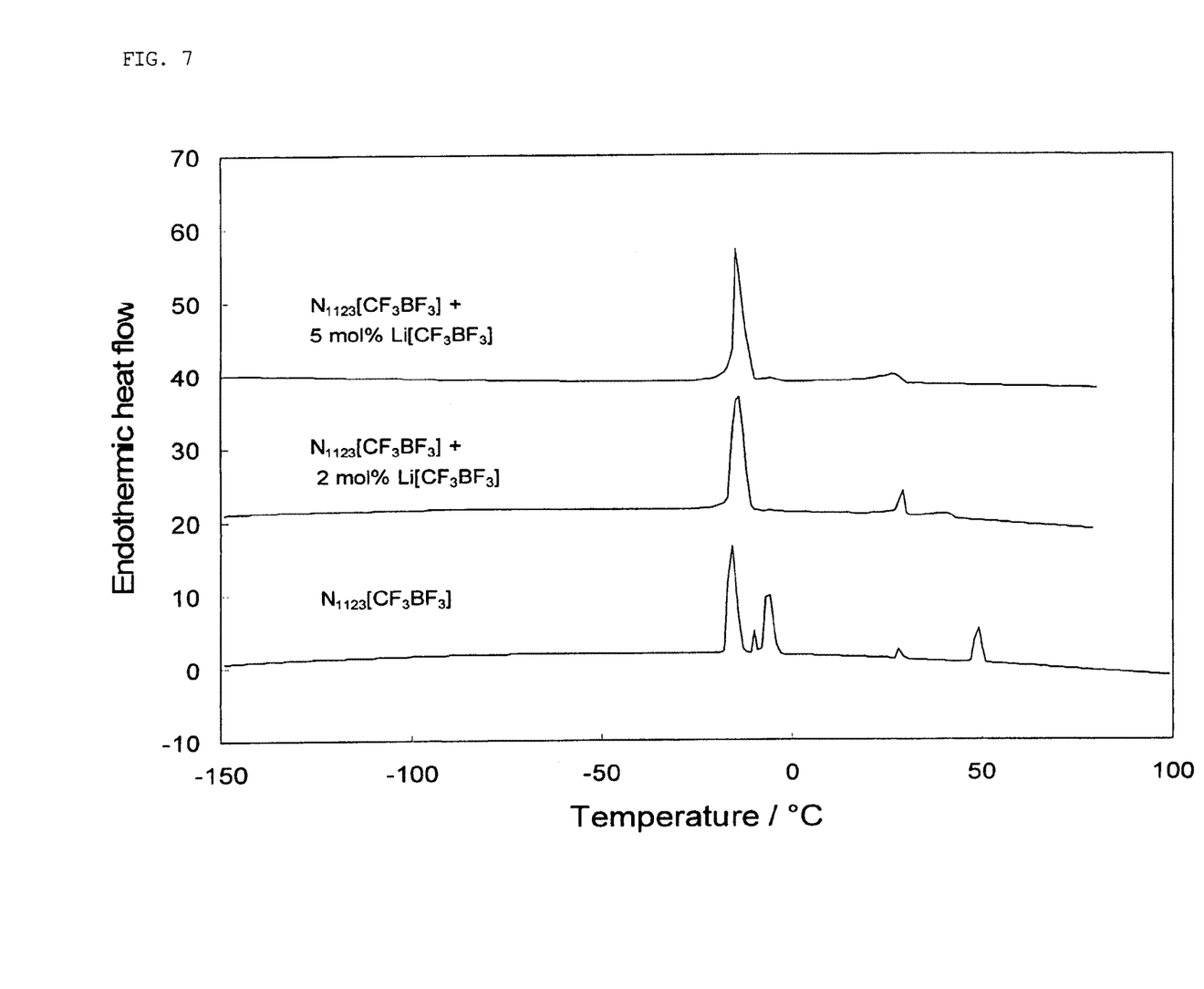
FIG. 7 shows the DSC results of $N_{1123}$[$CF_3BF_3$].

The plastic crystal of the present invention containing a $[BF_3(CF_3)]$ salt, such as $N_{1123}[CF_3BF_3]$ and $Li[BF_3(CF_3)]$, exhibits a colorless transparent plastic crystalline phase as shown in FIG. 7. Therefore, it is suitably usable for an optical material, a display, etc., in which transparency is required.

Figure 8:
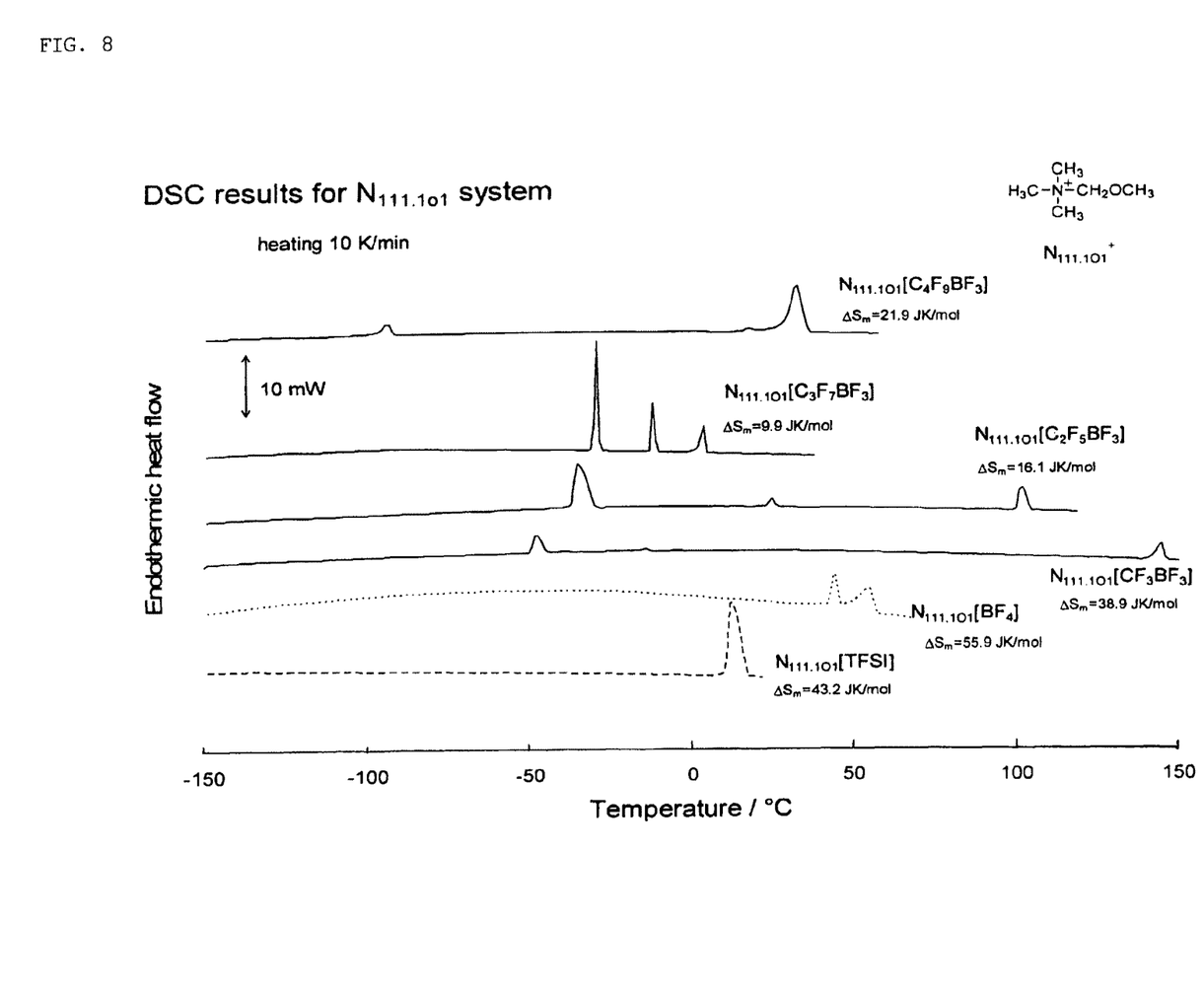
FIG. 8 shows the DSC results of various $N_{111.101}$ salts.
Figure 9:
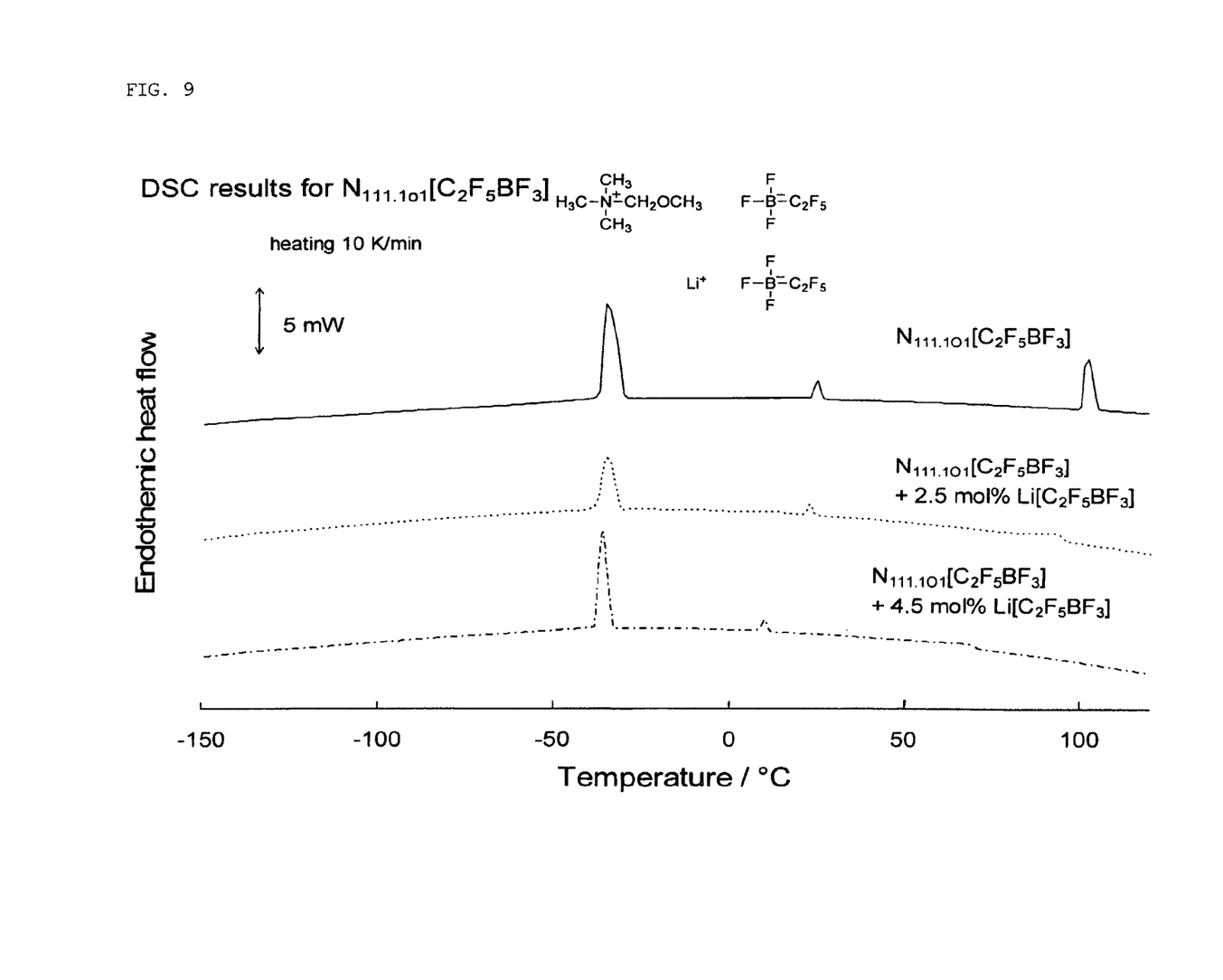
FIG. 9 shows the DSC results of $N_{111.101}$[$C_2F_5BF_3$].
Figure 10:
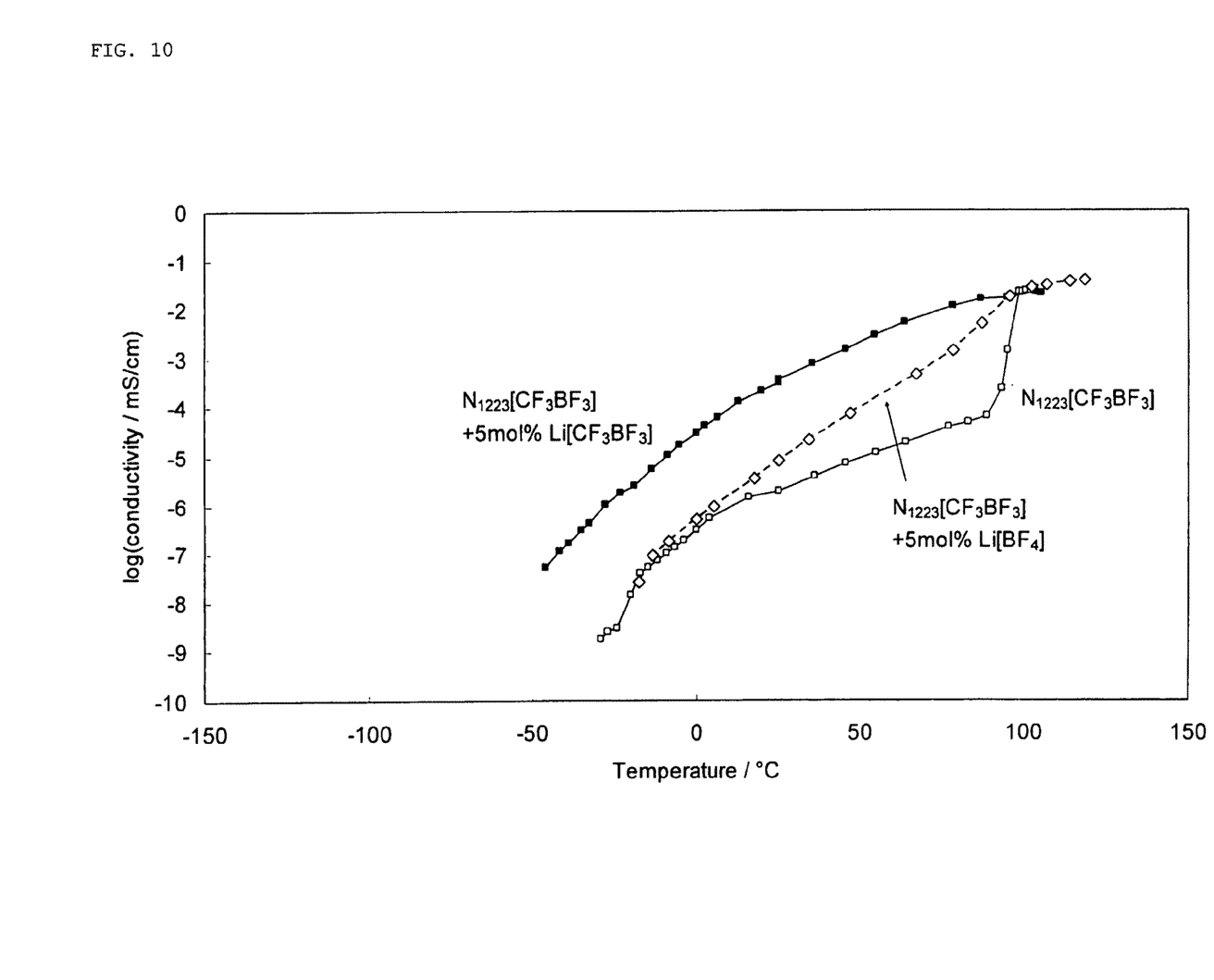
FIG. 10 shows the DSC results of $N_{1223}$[$CF_3BF_3$].
Figure 11:
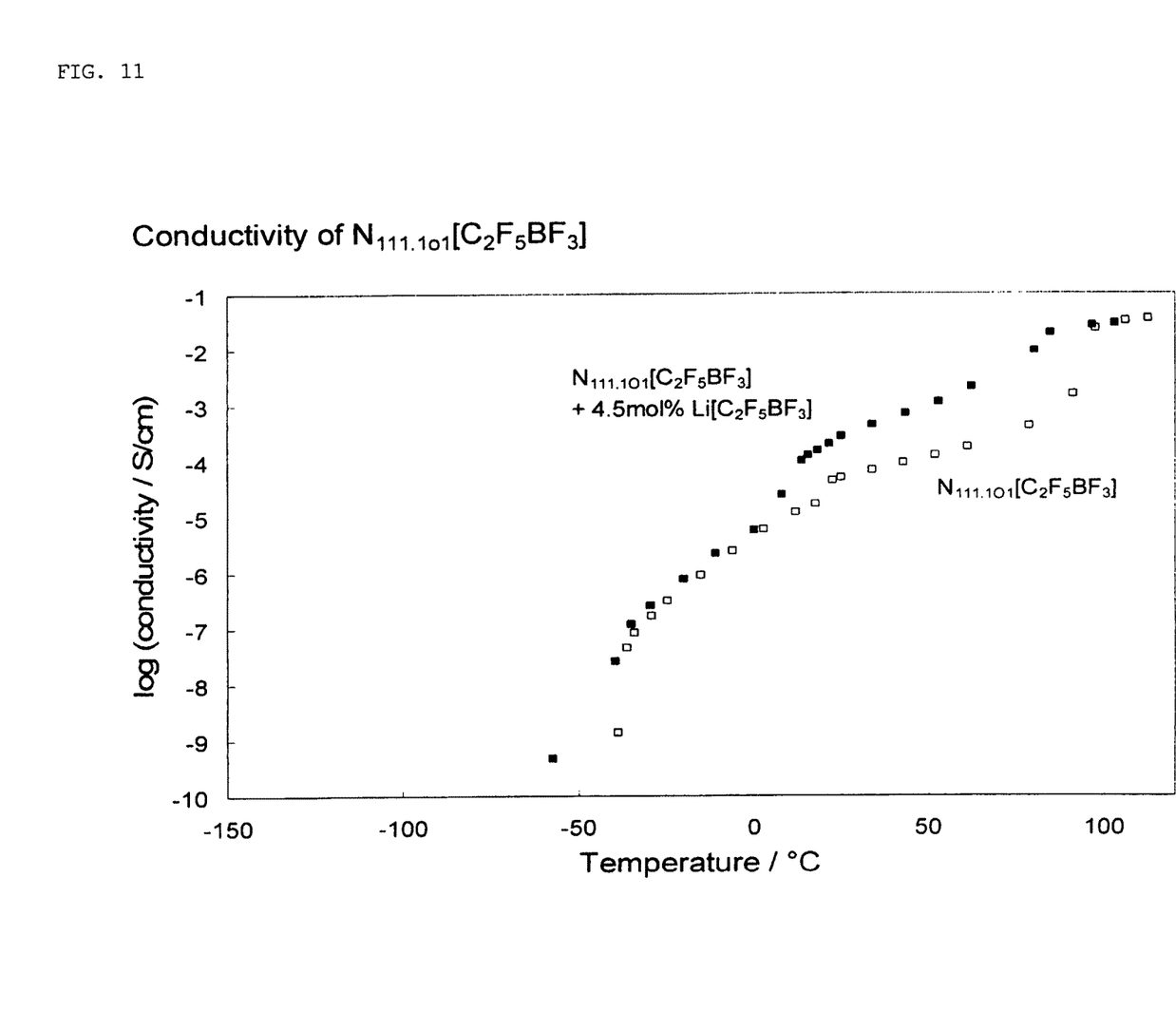
FIG. 11 shows the conductivity of $N_{111.101}$[$C_2F_5BF_3$].
Figure 12:
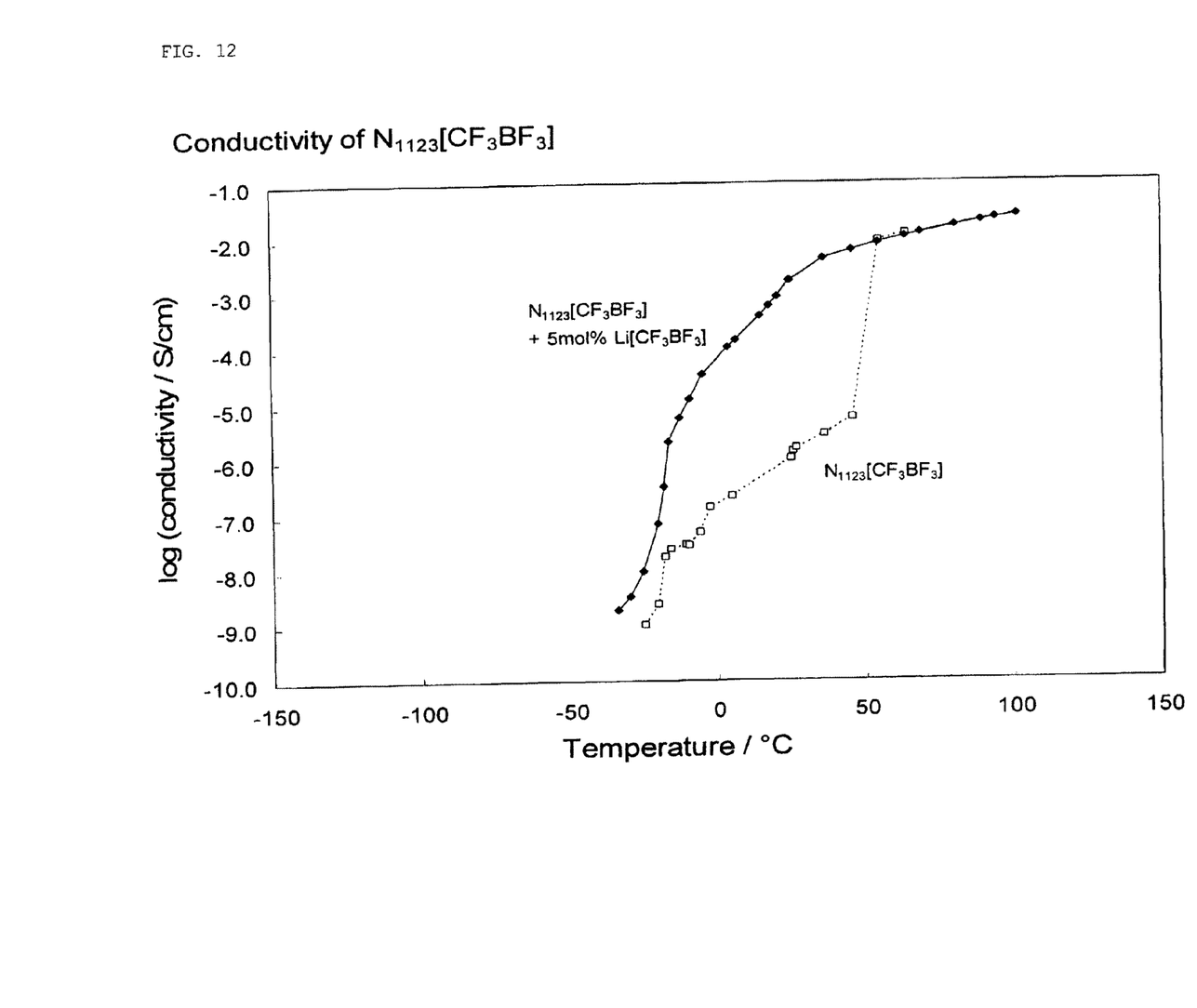
FIG. 12 shows the conductivity of $N_{1123}$[$CF_3BF_3$].
Figure 13:
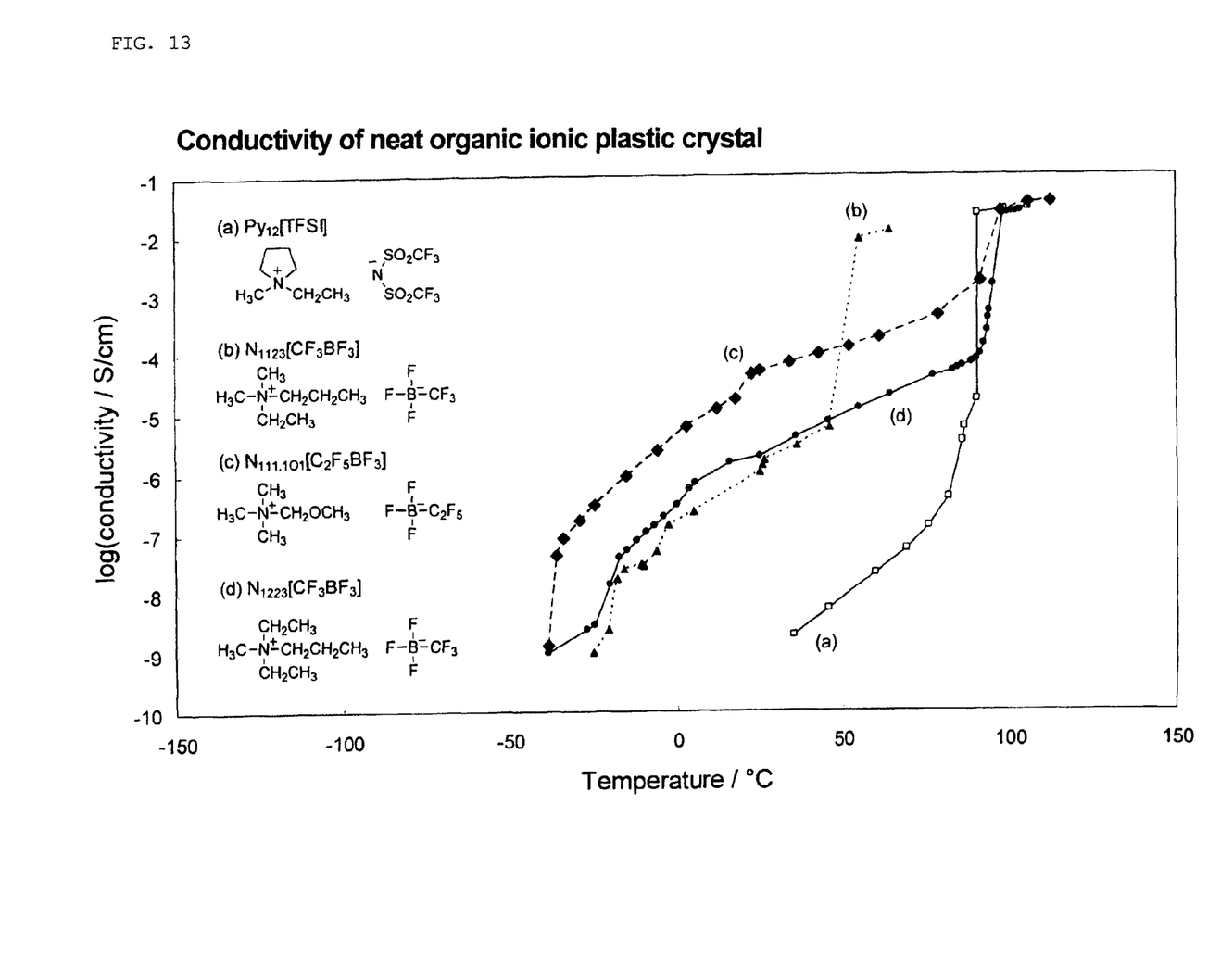
FIG. 13 shows the conductivity of the three compounds of the present invention and comparative compound Py12 [TFSI].

The plastic crystal of the present invention containing $N_{111.101}[C_2F_5BF_3]$ exhibits a colorless transparent plastic crystalline phase as shown in FIGS. 8 and 9, and therefore, is suitably usable for an optical material, a display, etc., in which transparency is required.

The plastic crystal of the present invention can raise the lithium ion conductivity by a multiple that ranges from several tens to several hundreds by being combined with a $[BF_3(CF_3)]$ salt represented by Formula (II), or a $[BF_3(C_2F_5)]$ salt represented by Formula (IIB) in a practical temperature range, e.g., −30° C. to 80° C. ($N_{1223}[CF_3BF_3]$), −20° C. to 50° C. ($N_{1123}[CF_3BF_3]$), or −40° C. to 100° C. ($N_{1123}[CF_3BF_3]$). In particular, its lithium ion conductivity at room temperature is improved to a practically usable level, such as $10^{-4}$ to $10^{-2}$ $Scm^{-1}$. Therefore, it is usable as a lithium ion battery (for example, a lithium secondary battery) and like electrochemical devices. To the compound represented by Formula (I), (IA), or (IB) of the present invention, $Li[BF_3(CF_3)]$, $Li[BF_3(C_2F_5)]$ or a like salt is added in an amount of 1 to 10 mol %, preferably 2 to 8 mol %, more preferably 2.5 to 7.5 mol %, still more preferably 4 to 6 mol %, and particularly preferably about 5 mol %. By selecting the amount of salt added within this range, it is possible to obtain a plastic crystalline phase that exists over a wide temperature range around room temperature, and to also improve the lithium ion conductivity.

The plastic crystal of the present invention combining a compound represented by Formula (I), (IA), or (IB) with a compound represented by Formula (III) or (IIIB) can be suitably used as an electrolyte for a solar cell, in particular, an electrolyte for a dye-sensitized solar cell. The amount of at least one compound represented by Formula (III) or (IIIB) added to the compound represented by Formula (I), (IA), or (IB) is generally about 10 to 50 mol %, preferably about 20 to 45 mol %, more preferably about 25 to 40 mol %, and particularly preferably about 30 to 36 mol %.

The plastic crystal of the present invention is highly soluble in electrolyte, noncombustible, and low in viscosity, and therefore it is suitably usable as an electrolyte having a high conductivity in a lithium secondary battery and like lithium batteries, electronic double layer capacitors, solar cells, electrochemical sensor devices, electrochemical display devices (electrochromic glass), etc.

EXAMPLES

The present invention is explained in detail below with reference to Examples.

Example 1

All operations for the preparation and measurement of a material sensitive to air were conducted in an argon-filled glove box (Miwa MDB-1.5-1000T, $H_2O$ and $O_2$<1 ppm). An NMR spectrum was recorded by a JEOL JNM AL400 spectrometer ($^1H$ at 399.65 MHz, $^{19}F$ at 376.05 MHz, $^{11}B$ at 128.15 MHz) using anhydrous acetone-$d_6$ as a solvent. Chemical shifts (d) in $BF_3.Et_2O$ were measured using TMS as an internal standard ($^1H$) and $CCl_3F$ as an external standard, respectively, in acetone-$d_6$ ($^{19}F$) and $CDCl_3$ ($^{11}B$).

$N_{1223}[CF_3BF_3]$ was prepared in the same manner as that disclosed in "Z.-B. Zhou, H. Matsumoto, K. Tatsumi, Chem. Eur. J. 11 (2005) 752". A lithium trifluoromethyl trifluoroborate-dimethyl carbonate complex ($Li[CF_3BF_3].DMC$, 1:1) was prepared in the same manner as used to prepare $Li[C_2F_5BF_3].DMC$, which is an analog thereof. Specifically, the lithium trifluoromethyl trifluoroborate-dimethyl carbonate complex was prepared in dimethyl carbonate (DMC) by metathesis reaction between $K[CF_3BF_3]$ and $LiBF_4$ (Z.-B. Zhou, M. Takeda, T. Fujii, M. Ue, J. Electrochem. Soc. 152 (2005) A351). Characterization data: $^1H$ NMR: d3.72 ppm (s, $OCH_3$ of DMC). $^{19}F$ NMR: d −74.8 (q, $^2J_{BF}$=32.4 Hz, 3F, $CF_3$), −156.2 ppm (q, $^1J_{BF}$=39.7 Hz, 3F, $BF_3$) $^{11}B$ NMR: d −0.47 ppm (qq, $^1J_{BF}$=39.0 Hz, $^2J_{BF}$=32.3 Hz). Anal. Calcd. for $C_4H_6BF_6LiO_3$: C, 20.6; H, 2.6; Li, 3.0. Found: C, 20.8; H, 2.7; Li, 3.0.

$N_{1123}[CF_3BF_3]$ was prepared in the same manner as described above except that $N_{1123}$ was used instead of $N_{1223}$.

$N_{111.101}[C_2F_5BF_3]$ was prepared in the same manner as described above except that $N_{111.101}$ was used instead of $N_{1223}$, and $[C_2F_5BF_3]$ was used instead of $[CF_3BF_3]$.

An Li-doped plastic crystalline electrolyte was prepared by melting an adequate amount of $N_{1223}[CF_3BF_3]$ or $N_{1123}[CF_3BF_3]$ together with $Li[CF_3BF_3].DMC$ at 100° C., or melting an adequate amount of $N_{111.101}[C_2F_5BF_3]$ with $Li[C_2F_5BF_3].DMC$ at 100° C.

The DMC in the Li-doped material was exhausted under a high vacuum condition at 80° C. for 5 hours. The complete removal of the DMC from the material was confirmed using $^1$H NMR (acetone-d6). When no peak of d 3.72 ppm attributable to the existence of DMC was detected, it was concluded that the DMC was completely exhausted.

Differential scanning calorimetry (DSC) was conducted using a Perkin Elmer Pyris 1 (see FIG. 2, FIG. 7, FIG. 8, and FIG. 9). A sample of about 10 mg was sealed in an aluminum pan and scanned at the rate of 10° C. min$^{-1}$ under helium gas flow. The data regarding the phase transition temperature were obtained at the maximum peak during heating.

Conductivity was measured with a commercially available conductivity cell formed of two parallel plating blacks (Radiometer analytical CDC-749). The cell constant was about 1.7 cm$^{-1}$ and the cell constant was calibrated before and after the measurement of each sample using a 0.01 M KCl aqueous solution at 25° C. The electroconductivity was calculated from Cole plots obtained by ac impedance spectroscopy in the frequency range of from 10 mHz to 10 MHz using a Schlumberger SI 1260 impedance/gain phase analyzer. The temperature of the cell was controlled by an aluminum block bath. Before the measurement, each sample sealed in the cell was melted at a temperature not lower than the above-mentioned melting point, and then slowly cooled to −60° C. at the rate of 0.5° C. min$^{-1}$. Electroconductivity was measured during heating at the heating rate of 0.2° C. min$^{-1}$. The data at each temperature were obtained by measuring after annealing the sample for 1 to 2 hours (FIG. 3, FIG. 10, FIG. 11, FIG. 12, and FIG. 13).

Figure 4:
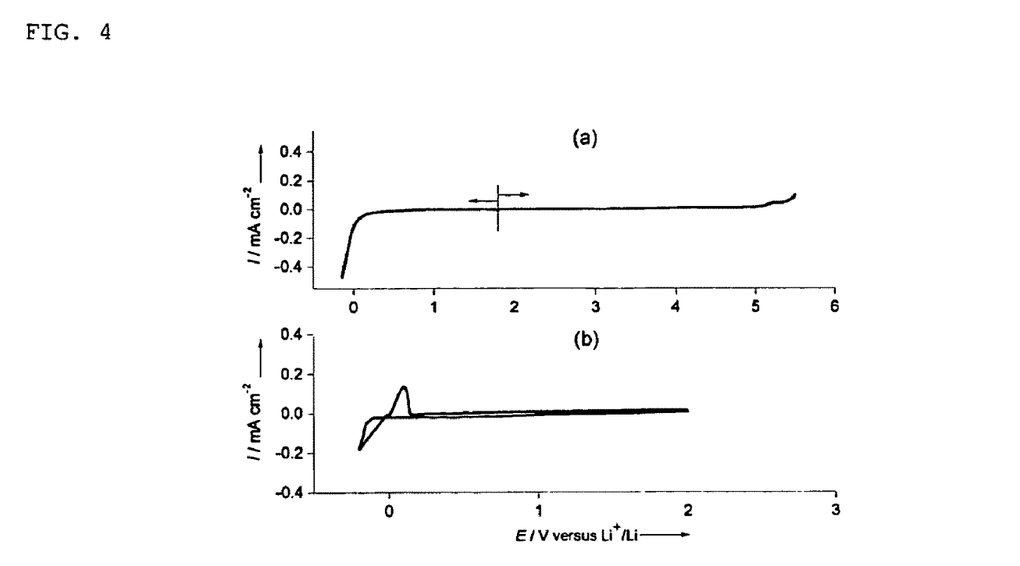
FIG. 4 shows a voltammogram obtained from the first scan of a plastic crystal $N_{1223}$[$CF_3BF_3$] to which 5 mol % Li[$CF_3BF_3$] was doped at 25° C., with a scan speed of 5 mVs$^{-1}$; (a) Pt electrode (surface area: $2.0 \times 10^{-2}$ cm$^2$); (b) Ni electrode (surface area: $1.77 \times 10^{-2}$ cm$^2$); and Li foil were used as a counter electrode and a semi-reference electrode.

A linear sweep voltammogram and a cyclic voltammogram of an Li-doped plastic crystal in a solid state at 25° C. were measured using a computer-controlled electrochemical analyzer (ALS model 660A). A disk electrode of Pt and one of Ni, respectively, were used as the working electrode for the linear sweep voltammogram and the cyclic voltammogram. Li foil was used as a counter electrode and a semi-reference electrode. Prior to measurement, each sample was melted at a temperature higher than its melting point to obtain favorable surfaces for an electrolyte and an electrode, and then slowly cooled to 25° C. (FIG. 4).

Figure 6:
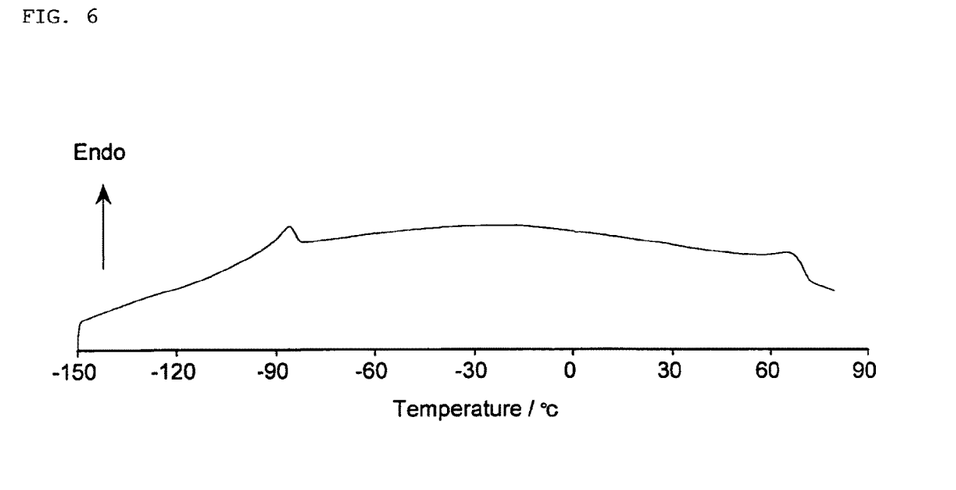
FIG. 6 is a DSC chart of $N_{1223}$-$CF_3BF_3$ (0.67) I (0.23) $I_3$ (0.1).

A DSC chart of $N_{1223}$-$CF_3BF_3$ (0.67) I (0.23) $I_3$ (0.1) (programming rate 10° C./min) is attached as FIG. 6.

Results

The material of the present invention containing pure $N_{1223}$ [$CF_3BF_3$] or $N_{1123}$[$CF_3BF_3$] with Li[$CF_3BF_3$], and the material of the present invention containing $N_{111.101}$[$C_2F_5BF_3$] exhibited remarkable flexibility at room temperature similar to that of a soft polymer.

As shown in FIG. 1, by melting this material ($N_{1223}$ [$CF_3BF_3$], $N_{1123}$[$CF_3BF_3$] or $N_{111.101}$[$C_2F_5BF_3$]) on the surface of a PTFE plate, a colorless transparent self-standing film was easily obtained. The resulting self-standing film did not break even when it was considerably bent or stretched.

Such excellent mechanical characteristics of these materials are desirable for the preparation of a solid electrolyte having dimensional stability. According to one preferable embodiment, by doping with 1 to 10 mol %, and preferably 2.5 to 5 mol %, of Li[$CF_3BF_3$], or Li[$C_2F_5BF_3$], a transparent, colorless and flexible solid material having satisfactory mechanical strength can be obtained. The resulting Li-doped material takes the form of a self-standing film at room temperature.

Figure 2:
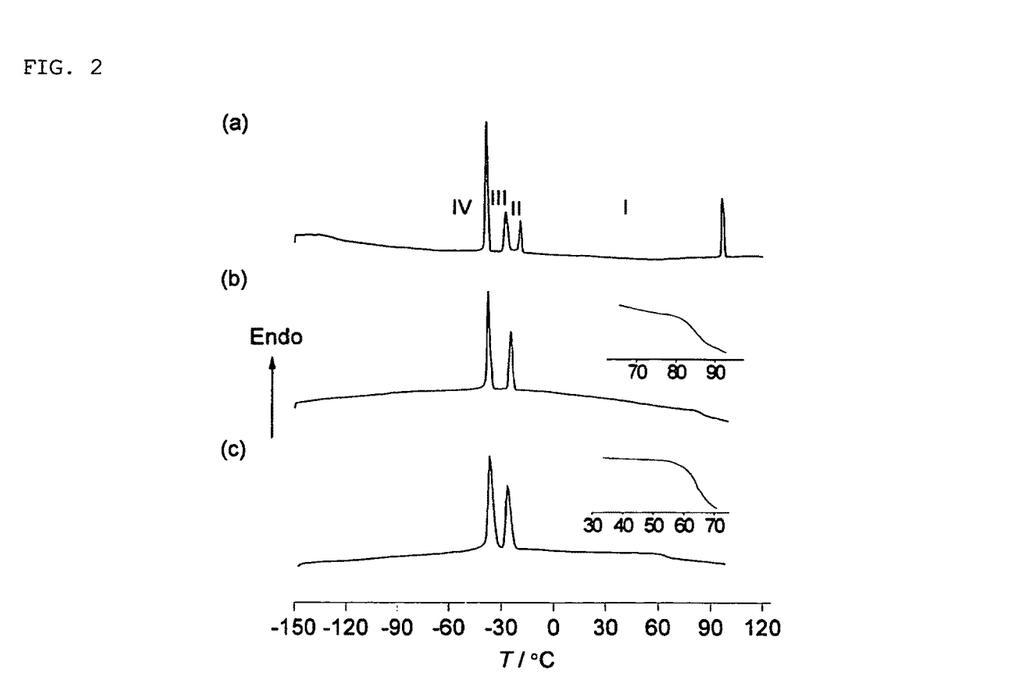
FIG. 2 shows the DSC curves of plastic crystal $N_{1223}$[$CF_3BF_3$] to which various amounts of Li[$CF_3BF_3$] were doped, wherein (a) indicates without doping (only $N_{1223}$[$CF_3BF_3$]), (b) indicates 2.5 mol % Li[$CF_3BF_3$] doping, and (c) indicates 5 mol % Li[$CF_3BF_3$] doping. The inserted graphs are enlarged views of the DSC curves around the melting points.

FIG. 2 shows DSC curves during the heating of non-doped $N_{1223}$[$CF_3BF_3$] and Li[$CF_3BF_3$]-doped $N_{1223}$[$CF_3BF_3$]. Table 1 shows data characteristic of a phase transition. Similarly, FIG. 7 shows DSC curves during the heating of non-doped $N_{1123}$[$CF_3BF_3$] and Li[$CF_3BF_3$]-doped $N_{1123}$ [$CF_3BF_3$]. FIG. 9 shows DSC curves during the heating of non-doped $N_{111.101}$[$C_2F_5BF_3$] and Li[$C_2F_5BF_3$]-doped $N_{111.101}$[$C_2F_5BF_3$]. Furthermore, FIG. 8 shows DSC curves of $N_{111.101}$ salts with various anions.

TABLE 1

Phase Transition of Non-doped and Li-doped Plastic Crystal

| Sample | $T_{s-s}$ (° C.)$^a$ | $\Delta H_{s-s}$ (kJ mol$^{-1}$)$^b$ | $T_m$ (° C.)$^c$ | $\Delta S_m$ (JK$^{-1}$ mol$^{-1}$)$^d$ |
|---|---|---|---|---|
| $N_{1223}$[$CH_3BF_3$] | −38 (IV→III) | 6.70 | 95 | 7.4 |
|  | −28 (III→II) | 2.52 |  |  |
|  | −20 (II→I) | 1.46 |  |  |
| $N_{1223}$[$CH_3BF_3$] + 2.5 mol % Li[$CH_3BF_3$] | −38 −26 | 6.57 4.01 | 85 | 3.1 |
| $N_{1223}$[$CH_3BF_3$] + 5 mol % Li[$CH_3BF_3$] | −37 −27 | 6.61 4.03 | 60 | 2.8 |

$^a$Solid-Solid Transition
$^b$Solid-Solid Transition Entropy
$^c$Melting Point
$^d$Melting Entropy When $N_{1223}$[$CF_3BF_3$] was doped with 2.5 mol % or 5 mol % Li[$CF_3BF_3$], transitions from phase IV to phase III (−38° C.) and from phase III to phase II (−28° C.) became slightly broader, and transition from phase II to phase I (−20° C.) became very small.

When $N_{1223}$[$CF_3BF_3$] was doped with 2.5 mol % Li[$CF_3BF_3$], its melting point became approximately 85° C. When $N_{1223}$[$CF_3BF_3$] was doped with 5 mol % Li[$CF_3BF_3$], its melting point became approximately 60° C. (FIGS. 2b and 2c). As shown in Table 1, the Li-doped materials exhibited extremely lower $DS_m$ values, i.e., less than 3.5 J mol$^{-1}$K$^{-1}$, than that of the non-doped material. This indicates that such material has a property similar to that of liquid, i.e., a fast ion rotation and/or orientation velocity. Similar results were obtained for $N_{1123}$[$CF_3BF_3$] and $N_{111.101}$[$C_2F_5BF_3$].

The Li-doped materials are soft and flexible at room temperature, but they are not fluids at temperatures that are below their melting points. Furthermore, no peaks attributable to glass transition or crystallization/melting were observed in the Li-doped materials during DSC scanning. This indicates that 1) the existence of a eutectic phase may be excluded in an Li-doped system, 2) the structure of the plastic crystalline phase matrix does not fundamentally change by being doped with 1 to 10 mol %, or, in particular, 2.5 to 5 mol % (or 2 to 5 mol %) of Li, i.e., the plastic crystalline phase is a true solid solution.

FIGS. 3 and 10 to 13 show the ion conductivity of doped plastic crystalline materials based on a function of temperature. When a compound represented by Formula (I) was doped with 2.5 mol % (0.1 mol/kg) or 5 mol % (0.2 mol/kg) Li[$CF_3BF_3$], its electroconductivity remarkably increased by more than ten times across the entire temperature range over which a plastic crystalline phase existed. A similar increase in electroconductivity was also observed in the compounds represented by Formulae (IA) and (IB). Having a liquid-like property (as implied from the extremely low melting entropy (see Table 1)) is advantageous for a fast ion transition in the plastic crystalline phase of a Li-doped material, and serves an important role in remarkably increasing electroconductivity.

Figure 3:
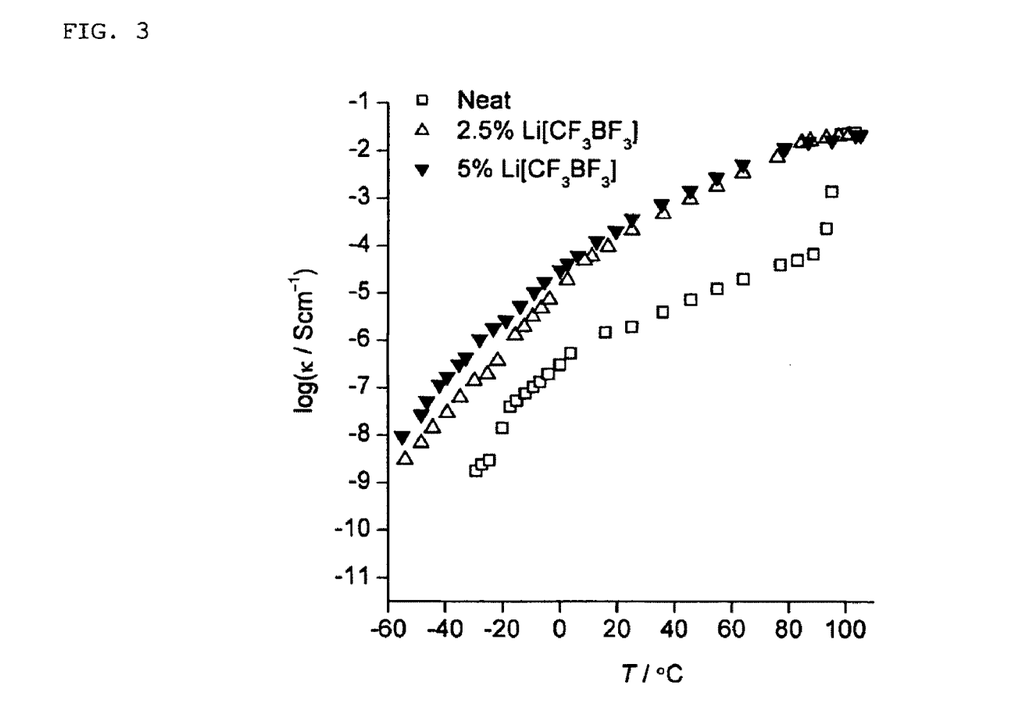
FIG. 3 is a graph showing the relationship between temperature and electroconductivity for a plastic crystal $N_{1223}$[$CF_3BF_3$] without Li[$CF_3BF_3$] doping, and a plastic crystal $N_{1223}$[$CF_3BF_3$] to which 2.5 mol % or 5 mol % Li[$CF_3BF_3$] was doped.

The electroconductivity was increased from $1.9 \times 10^{-6}$ Scm$^{-1}$ to $2.1 \times 10^{-4}$ Scm$^{-1}$ and to $3.7 \times 10^{-4}$ Scm$^{-1}$, respectively, at 25° C. (FIG. 3). These electroconductivity values (at 25° C.) are higher by one to two orders of magnitude than that of a plastic crystal of lithium salt-doped pyrrolidinium TFSI and lithium salt-doped pyrazolium TFSI, which have been extensively studied. The electroconductivity of the Li[$CF_3BF_3$]-doped compound of the present invention is almost equal to that of a lithium salt/ionic liquid martial, such as LiTFSI/N-methyl-N-propylpyrrolidinium-TFSI (0.3 mol/kg, $7.3 \times 10^{-4}$ Scm$^{-1}$ at 25° C.). The solid phase electroconductivity of the plastic crystalline phase, when 2.5 mol % and 5 mol % Li[$CF_3BF_3$] were doped, respectively, increased to $1.8 \times 10^{-3}$ Scm$^{-1}$ at 55° C. and to $3.7 \times 10^{-3}$ Scm$^{-1}$ at 45° C.

Most importantly, a material to which 5 mol % (0.2 mol kg$^{-1}$) Li[$CF_3BF_3$] was doped exhibited as high as $10^{-4}$ to $10^{-3}$ Scm$^{-1}$ solid phase electroconductivity at 10 to 50° C., i.e., the temperature range over which a plastic crystalline phase exists. Such a high solid-phase electroconductivity is observed within the temperature range wherein this material is probably most often used, i.e., the most practical temperature range. Therefore, this characteristic is very advantageous when the material is used as a solid electrolyte for a Li battery.

The electrochemical stability of the Li-doped plastic crystalline electrolyte was analyzed with straight-line sweep voltammetry. FIG. 4a shows the straight-line sweep voltammetry of 5 mol % Li[$CF_3BF_3$]-doped plastic crystalline electrolyte measured on a solid phase Pt electrode at 25° C.

This material has a wide electrochemical window for a 0 to 5.5 V versus Li$^+$/Li semi-reference electrode. The stability of the cathode and anode Li-doped material of a solid phase is almost the same as that of a liquid salt (ionic liquid) that contains quaternary ammonium and [$CF_3BF_3$]$^-$, and is comparable to that of a TFSI$^-$ salt. FIG. 4b shows a cyclic voltammogram of the Li-doped material measured on Ni electrode of a solid phase at 25° C. In this material, a pair of peaks were observed which characterize the reduction of Li$^+$ ions and the reoxidation of Li metal in 0 V versus Li$^+$/Li. This is the first example of Li deposition/melting in a true solid solution at room temperature based on an ionic plastic crystalline electrolyte.

This result clearly indicates that an Li-doped plastic crystalline electrolyte is usable as a solid electrolyte for a Li battery.

The melting point of iodine compound-doped $N_{1223}$-$CF_3BF_3$ (0.67) I (0.23) $I_3$ (0.1)(FIG. 6) calculated based on the tangential line on the peak was 50° C. The melting enthalpy obtained based on this melting peak area was 1.9 kJ mol$^{-1}$, and the melting entropy was $\Delta Sm=5.7$ J mol$^{-1}$ K$^{-1}$, which satisfies Timmerman's requirement (<20 J mol$^{-1}$ K$^{-1}$). Therefore, a salt having this composition is also a plastic crystal, which is definitely not a eutectic mixture of $N_{1223}$[$CF_3BF_3$] with $N_{1223}$[I] or $N_{1223}$[$I_3$].

$N_{1223}$[$CF_3BF_3$] and $N_{1123}$[$CF_3BF_3$] have similar properties. The present inventors newly found that $N_{111.101}$[$C_2F_5BF_3$] is also a plastic crystal.

4. Results:

N, N-diethyl-N-methyl-N-(n-propyl) ammonium trifluoromethyl trifluoroborate ($N_{1223}$[$CF_3BF_3$]), which is a novel organic ionic plastic crystal of the present invention, has an excellent film formation ability, a low-melting entropy, and the highest temperature phase covering a wide range of ambient temperatures from −21 to 95° C. Therefore, $N_{1223}$[$CF_3BF_3$] can be used to prepare a Li-ion conductive plastic crystalline electrolyte as a matrix to which a small amount of Li[$CF_3BF_3$] is doped. $N_{1223}$[$CF_3BF_3$] has a solid electroconductivity of $10^{-4}$ to $10^{-3}$ Scm$^{-1}$ at ambient temperatures, which is the highest solid electroconductivity value among those of various Li-doped materials. Deposition/melting of solid phase Li based on the Li-doped plastic crystalline electrolyte was observed at 25° C. These results indicate the feasibility of not only obtaining a solid phase lithium battery using an ionic plastic crystalline electrolyte but also of providing novel ionic plastic crystals modified for various applications.

($N_{1123}$[$CF_3BF_3$]) and $N_{111.101}$[$C_2F_5BF_3$] also exhibited excellent results as novel ionic plastic crystals.

Example 2

Figure 5:
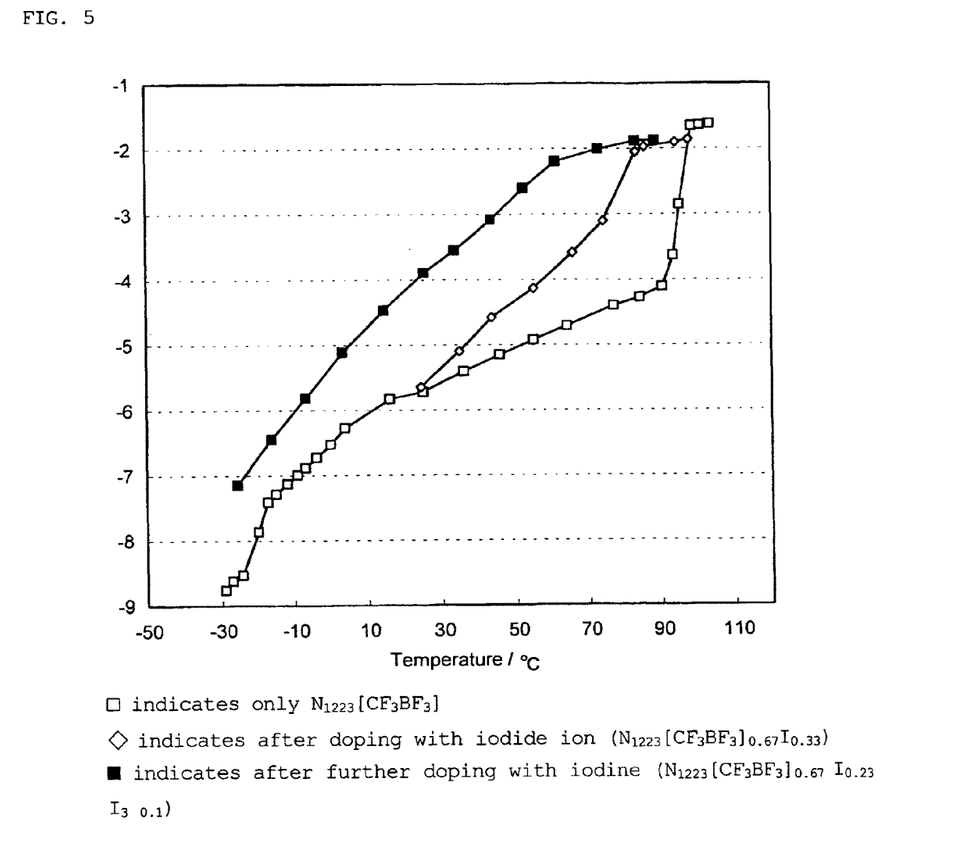
FIG. 5 is a graph showing the relationship between temperature and electroconductivity for only $N_{1223}$[$CF_3BF_3$] (☐), after doping with iodide ions (◇; $N_{1223}$[$CF_3BF_3$]$_{0.67}$I$_{0.33}$), and after further doping with iodine (■; $N_{1223}$[$CF_3BF_3$]$_{0.67}$ I$_{0.23}$ $I_3$ $_{0.1}$).

FIG. 5 shows the results of iodine doping, wherein (☐) indicates only $N_{1223}$[$CF_3BF_3$]: (◇; $N_{1223}$[$CF_3BF_3$]$_{0.67}$I$_{0.33}$) indicates after doping with iodide ions: and (■; $N_{11223}$[$CF_3BF_3$]$_{0.67}$ I$_{0.23}$ $I_3$ $_{0.1}$) indicates after further doping with iodine. As is clear from the results shown in FIG. 5, a plastic crystal to which iodide ions were further doped is usable as a solid electrolyte for a dye-sensitized solar cell.

The invention claimed is:

1. A plastic crystal containing a compound represented by Formula (I) or (IA) below:

and at least one [BF$_3$(CF$_3$)] salt represented by Formula (II):

$$M^{n+}[BF_3(CF_3)^-]_n \quad (II)$$

wherein M is an alkaline metal, alkaline earth metal, aluminum or H; and when M is an alkaline metal or H, n is 1; when M is an alkaline earth metal, n is 2; and when M is aluminum, n is 3.

2. The plastic crystal according to claim 1, which contains 1 to 10 mol % of the [BF$_3$(CF$_3$)] salt.

3. The plastic crystal according to claim 1, which contains 2.5 to 5 mol % of the [BF$_3$(CF$_3$)] salt.

4. A plastic crystal comprising a compound represented by Formula (I) or (IA) below:

and a compound represented by Formula (III) or (IIIA) below:

$$N^+(CH_3)(CH_2CH_3)_2(CH_2CH_2CH_3)\cdot X^- \quad (III)$$

$$N^+(CH_3)_2(CH_2CH_3)(CH_2CH_2CH_3)\cdot X^- \quad (IIIA)$$

wherein X is a hydroxide ion, halogenated compound ion, or pseudohalogen ion.

5. The plastic crystal according to claim 4, which contains 10 to 50 mol % of a compound represented by Formula (III) or (IIIA).

6. A plastic crystal represented by Formula (IB) below:

7. The plastic crystal according to claim 6, which comprises a compound represented by Formula (IB) below:

and at least one [BF$_3$(C$_2$F$_5$)] salt represented by Formula (IIB):

$$M^{n+}[BF_3(C_2F_5)^-]_n \quad (IIB)$$

wherein M is an alkaline metal, alkaline earth metal, aluminum or H; and when M is an alkaline metal or H, n is 1; when M is an alkaline earth metal, n is 2; and when M is aluminum, n is 3.

8. The plastic crystal according to claim 7, which comprises 1 to 10 mol % of the [BF$_3$(C$_2$F$_5$)] salt.

9. The plastic crystal according to claim 7, which comprises 2.5 to 5 mol % of the [BF$_3$(C$_2$F$_5$)] salt.

10. A plastic crystal comprising a compound represented by Formula (IB) below:

and a compound represented by Formula (IIIB):

$$N^+(CH_3)_3(CH_2OCH_3)\cdot X^- \quad (IIIB)$$

wherein X represent a hydroxide ion, halogenated compound ion, or pseudohalogen ion.

11. The plastic crystal according to claim 10, which comprises 10 to 50 mol % of the compound represented by Formula (IIIB).

12. An electrochemical device comprising a plastic crystal of any one of claims 1 to 11.

13. An electrolyte for a dye-sensitized solar cell comprising a plastic crystal of claim 4, 5, 10 or 11.

* * * * *